(12) United States Patent
Thornton

(10) Patent No.: US 6,325,064 B1
(45) Date of Patent: Dec. 4, 2001

(54) DEVICE FOR IMPROVING BREATHING AND METHOD OF FITTING SAME

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 0 days.

(21) Appl. No.: 09/396,986

(22) Filed: Sep. 15, 1999

(51) Int. Cl.[7] ................................... A61M 16/00

(52) U.S. Cl. ............... 128/204.18; 128/206.29; 128/201.26; 128/848

(58) Field of Search ............ 128/204.18, 206.29, 128/200.24, 201.18, 201.26, 860, 848, 859

(56) References Cited

U.S. PATENT DOCUMENTS

| | | | |
|---|---|---|---|
| 4,906,234 | 3/1990 | Voychehovski | 604/79 |
| 5,042,478 | 8/1991 | Kopala et al. | 128/207.18 |
| 5,558,090 | 9/1996 | James | 128/207.18 |
| 5,687,715 | 11/1997 | Landis et al. | 128/207.18 |
| 6,109,265 * | 8/2000 | Frantz et al. | 128/848 |

OTHER PUBLICATIONS

English translation of German Patent Specification No. 295 06 512.5 (Erkodent) Erich Kopp GmbH) Apr. 11, 1995.

* cited by examiner

*Primary Examiner*—John G. Weiss
*Assistant Examiner*—V. Srivastava
(74) *Attorney, Agent, or Firm*—Baker Botts L.L.P.

(57) ABSTRACT

A device (10) for improving the breathing of a user includes an upper arch (12) having a plate (20) and adapted to receive at least some of the user's upper teeth and a lower arch (14) adapted to receive at least some of the user's lower teeth. A line (22) removably engages the lower arch (14) and moves between the plate (20) and the upper arch (12) to adjust the forward position of the lower arch (14) when the line (22) is not secured between the plate (20) and the upper arch (12). The plate (20) secures the line (22) between the plate (20) and the upper arch (12) to at least temporarily fix the forward position of the lower arch (14). Alternatively, an adjustor (40) coupled to the upper arch (12) includes a shaft (46) having a forwardly directed channel to receive a portion of the line (22) that is inserted into the channel. At least a portion of the adjustor (40) can be rotated in a first direction to wrap the line (22) around the shaft (46) and thereby adjust the position of the lower arch (14) forward.

28 Claims, 4 Drawing Sheets

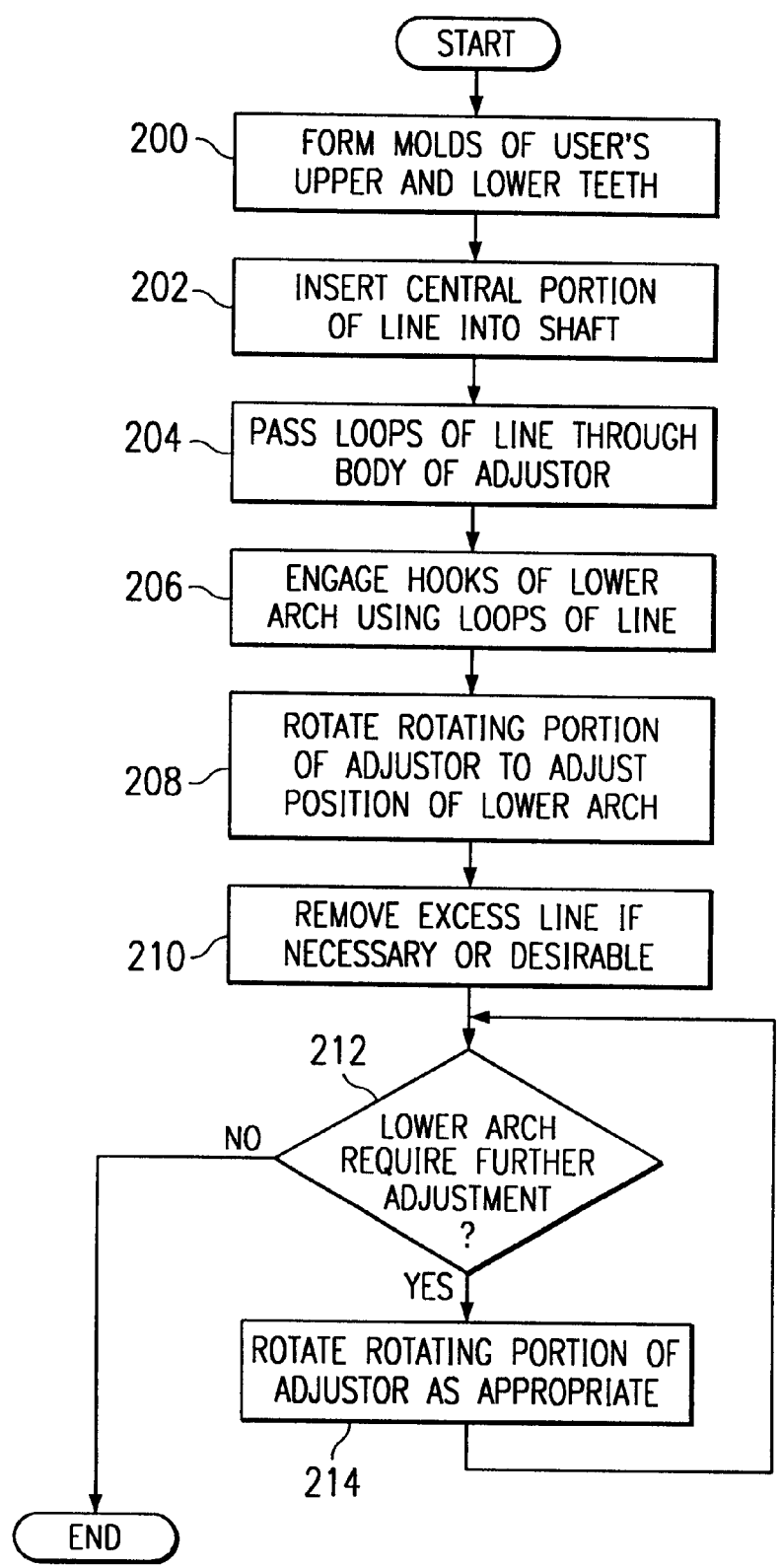

DEVICE FOR IMPROVING BREATHING AND METHOD OF FITTING SAME

CROSS-REFERENCE TO RELATED APPLICATIONS

This application is related to U.S. application Ser. No. 08/837,418, filed Apr. 16, 1997 by W. Keith Thornton and entitled "Device and Method for Improving Breathing," now U.S. Pat. No. 5,954,048, which is a continuation-in-part of U.S. application Ser. No. 08/582,526, filed Jan. 3, 1996, by W. Keith Thornton and entitled "Device for Improving Breathing," now abandoned, which is a continuation-in-part of U.S. application Ser. No. 08/253,949, filed Jun. 3, 1994, by W. Keith Thornton and entitled "Combination Face Mask and Dental Device for Improved Breathing During Sleep," now U.S. Pat. No. 5,537,994. This application is also related to U.S. application Ser. No. 09/290,512, filed Apr. 12, 1999 by W. Keith Thornton and entitled "Device for Improving Breathing," pending, which is a continuation of U.S. application Ser. No. 08/878,998, filed Jun. 19, 1997, by W. Keith Thornton and entitled, "Device for Improving Breathing," now U.S. Pat. No. 5,983,892, which is a continuation of U.S. application Ser. No. of 08/582,526.

This application is also related to U.S. application Ser. No. 08/594,904, filed Jan. 31, 1996, by W. Keith Thornton and entitled "Device for Improving Breathing," pending, which is a continuation of U.S. application Ser. No. 08/253,949. This application is also related to U.S. application Ser. No. 08/645,673, filed May 14, 1996, by W. Keith Thornton and entitled "Device for Improving Breathing," now U.S. Pat. No. 5,755,219, which is a continuation-in-part of U.S. application Ser. No. 08/253,949.

This application is further related to U.S. application Ser. No. 08/828,523, filed Mar. 31, 1997, by W. Keith Thornton and entitled "Apparatus for Prevention of Snoring and Improved Breathing During Sleep," pending, which is a continuation of U.S. application Ser. No. 08/363,639, filed Dec. 24, 1994, by W. Keith Thornton and entitled "Apparatus for Prevention of Snoring and Improved Breathing During Sleep," now abandoned, which is a continuation of U.S. application Ser. No. 08/129,598, filed Sep. 29, 1993, by W. Keith Thornton and entitled "Apparatus for Prevention of Snoring and Improved Breathing During Sleep," now U.S. Pat. No. 5,427,117. This application is further related to U.S. application Ser. No. 08/410,325, filed Mar. 24, 1995, by W. Keith Thornton and entitled "Apparatus for Prevention of Snoring and Improved Breathing During Sleep," now U.S. Pat. No. 5,566,683, which is a continuation-in-part of U.S. application Ser. No. 08/129,598.

This application is additionally related to U.S. application Ser. No. 08/787,529, filed Jan. 21, 1997, by W. Keith Thornton and entitled "Method and Apparatus for Adjusting a Dental Device," pending, which is a continuation of U.S. application Ser. No. 08/435,277, filed May 5, 1995, by W. Keith Thornton and Andrew O. Jamieson and entitled "Method and Apparatus for Adjusting a Dental Device," now abandoned, which is a continuation of U.S. application Ser. No. 08/218,719, filed Mar. 24, 1994, by W. Keith Thornton and Andrew O. Jamieson and entitled "Method and Apparatus for Adjusting a Dental Device," now abandoned. This application is additionally related to U.S. application Ser. No. 08/501,437, filed Sep. 18, 1995, by W. Keith Thornton and Andrew O. Jamieson and entitled "Apparatus for Adjusting a Dental Device," now U.S. Pat. No. 5,678,567, which is a continuation of U.S. application Ser. No. 08/435,277.

TECHNICAL FIELD OF THE INVENTION

This invention relates generally to medical, dental, and other oral appliances, and more particularly to a device for improving breathing and a method of fitting the same.

BACKGROUND OF THE INVENTION

Many people experience breathing problems, which may result in difficulty sleeping, in snoring, or in other more serious conditions such as obstructive sleep apnea. One treatment for such breathing disorders involves inserting a device into a user's mouth to extend the users lower jaw forward. By extending the user's lower jaw forward, such a device opens the user's breathing passage more fully and allows the user to breathe more easily through the user's nose and mouth.

As technology advances and users continue to demand increased performance, comfort, and ease of use, previous devices for improving breathing are increasingly inadequate. Previous devices for improving breathing include upper and lower arches connected using adjustment mechanisms that extend outside the user's mouth. Although these devices may treat some breathing problems, they are often unwieldy and lack the customizability, adjustability, and comfort necessary to serve a variety of users and treatment requirements. Because these devices extend outside of the user's mouth, the user's mouth is not allowed to substantially close, the user's breathing passage may be obstructed, and the users mouth may become excessively dry. Furthermore, adjustment mechanisms of previous devices often interfere with the natural position of the user's tongue or impinge on other soft tissues inside the user's mouth. Moreover, discomfort associated with these devices may cause users to use these devices less frequently than they otherwise would, further reducing performance. As a result of these and other deficiencies, previous devices for improving breathing are inadequate for the needs of many users.

SUMMARY OF THE INVENTION

According to the present invention, disadvantages and problems associated with previous devices and methods for improving breathing have been substantially reduced or eliminated.

In one embodiment of the present invention, a device for improving the breathing of a user includes an upper arch having a plate and adapted to receive at least some of the user's upper teeth and a lower arch adapted to receive at least some of the user's lower teeth. A line removably engages the lower arch and moves between the plate and the upper arch to adjust the forward position of the lower arch when the line is not secured between the plate and the upper arch. The plate secures the line between the plate and the upper arch to at least temporarily fix the forward position of the lower arch.

In another embodiment of the present invention, a device for improving the breathing of a user includes an outer plate, an upper arch having an inner plate and adapted to receive at least some of the user's upper teeth, and a lower arch adapted to receive at least some of the user's lower teeth. A line removably engages the lower arch and moves between the inner and outer plates to adjust the forward position of the lower arch when the line is not secured between the inner and outer plates. The outer plate secures the line between the outer plate and the inner plate to at least temporarily fix the forward position of the lower arch. When secured, the outer plate is substantially continuous with the surface of the upper arch. The device prevents the user's lips and inner mouth from being significantly disturbed and allows the user's mouth to be substantially closed when the device is inserted in the user's mouth.

In another embodiment of the present invention, a device for improving the breathing of a user includes a lower arch adapted to receive at least some of the user's lower teeth and a line having ends to removably engage the lower arch. An upper arch is adapted to receive at least some of the user's upper teeth. An adjustor coupled to the upper arch includes a shaft having a forwardly directed channel to receive a portion of the line that is inserted into the channel. At least a portion of the adjustor can be rotated in a first direction to wrap the line around the shaft and thereby adjust the position of the lower arch forward.

Important technical advantages of the present invention include the ease with which the device may be fitted and adjusted. After the line has removably engaged the lower arch and been passed between the plate and the remainder of the upper arch, the line may be moved as appropriate to adjustably position the lower arch forwardly relative to the upper arch. The line, and therefore the lower arch, may be readily adjusted in this manner as often as desired. Since all adjustments may be made, but are not required to be made, without removing the device from the user's mouth, adjusting the device is further simplified. The fitting of the device to the user's mouth, the initial adjustment of the lower arch, and any subsequent adjustments of the lower arch may be performed either by a clinical professional or by the user, in any suitable combination potentially decreasing the cost of the device to the user.

Another important technical advantage of the present invention is the comfort provided to the user. Appropriate portions of the adjustment mechanism, including the plate that secures the line to the upper arch and the mechanism that allows the line to engage the lower arch may be substantially continuous with the surface of the arches such that the user's lips and inner mouth are not significantly disturbed and the user's mouth may substantially close. Also, in one particular embodiment, the user's lower jaw is permitted to move laterally, further increasing the user's comfort without reducing the effectiveness of the device.

BRIEF DESCRIPTION OF THE DRAWINGS

For a more complete understanding of the present invention and for further features and advantages thereof, reference is now made to the following descriptions taken in conjunction with the accompanying drawings, in which:

FIGS. 5 and 6 are flow charts illustrating an exemplary method of fitting an oral appliance according to the present invention.

DETAILED DESCRIPTION OF THE INVENTION

Figure 1:
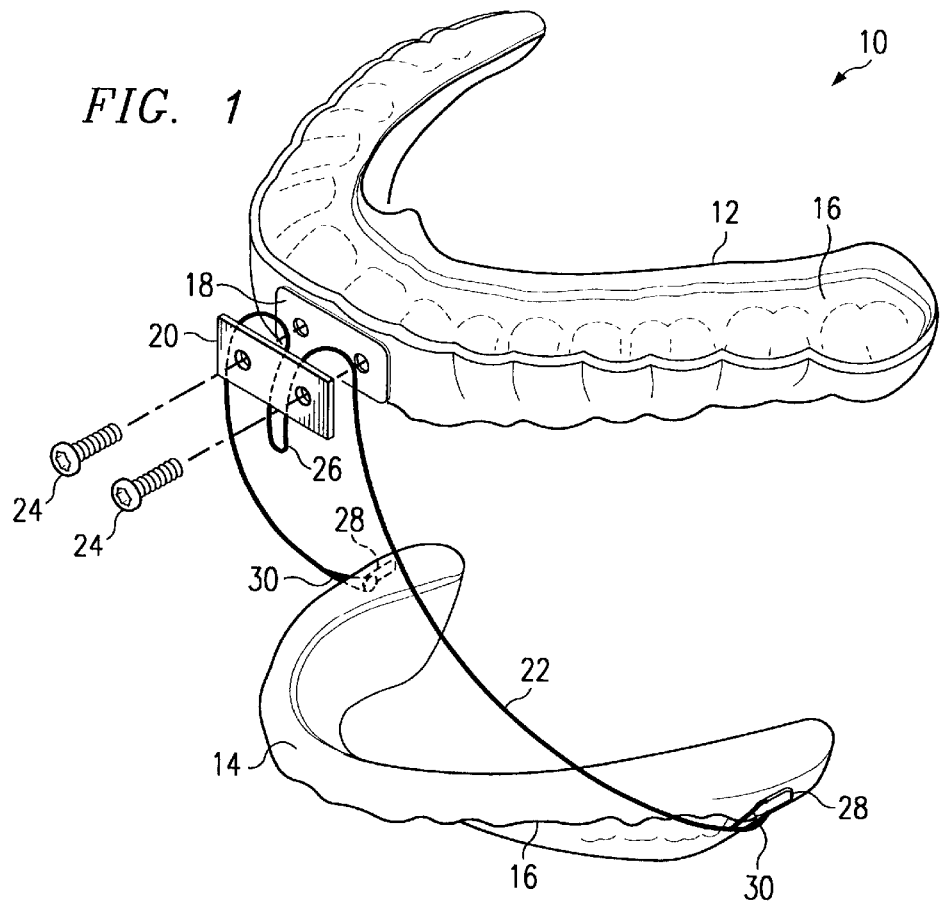
FIGS. 1 and 3 illustrates an exemplary devices for improving breathing according to the present invention.

FIG. 1 illustrates a device 10 for improving breathing that includes an upper arch 12 adapted to receive at least some of a user's upper teeth and a lower arch 14 adapted to receive at least some of the user's lower teeth. Device 10 may be considered a medical device, a dental device, or any other suitable type of oral appliance. In one embodiment, arches 12 and 14 are formed from a deformable material suitable for dental uses, such as methylmethacrylate or a polycarbonate resin thermoplastic such as LEXAN. Upper arch 12 and lower arch 14 are each adapted to receive a deformable material 16 in which molds of at least some of the user's upper and lower teeth, respectively, may be formed. Deformable material 16 may be an ethylene-vinyl acetate copolymer resin such as ELVAX, a polycaprolactone polymer such as TONE, or any other deformable material suitable for forming molds of a user's teeth.

In one embodiment, deformable material 16 is heated to approximately 150° F. or another temperature suitable to place deformable material 16 in its deformable state. Deformable material 16 may be coupled to upper arch 12 and lower arch 14 before or after being placed in its deformable state. Upper arch 12 and lower arch 14 are inserted into the user's mouth, separately or together, and the user bites down or otherwise presses at least some of the user's teeth into deformable material 16 to form a mold of at least some of the user's teeth. Upper arch 12 and lower arch 14 are removed from the user's mouth and allowed to further cool and harden. Arches 12 and 14 of device 10 may be customized in this manner by a clinical professional or by the user, potentially decreasing the cost of device 10 to the user. Upper arch 12 and lower arch 14 may be customized to fit the user's teeth before, during, or after assembly and adjustment of the remainder of device 10.

Upper arch 12 includes an inner plate 18 that may be integral to or separate from the remainder of upper arch 12. For example, inner plate 18 may be made of stainless steel, aluminum, or any other suitable material and may be embedded in or otherwise coupled to upper arch 12. Outer plate 20 may be releasably secured to inner plate 18 using two or any other suitable number of screws 24, although the present invention contemplates any appropriate fastener or other attachment mechanism. Line 22 may be a single or multiple stainless steel, monofilament, or other suitable lines. In a particular embodiment, line 22 includes multiple stainless steel lines woven together, braided together, or otherwise appropriately associated with each other. In operation, a central portion 26 of line 22 passes between inner plate 18 and outer plate 20 and may be adjustably secured between inner plate 18 and outer plate 20 to adjustably fix the position of line 22. Although line 22 is shown passing between outer plate 20 and inner plate 18 from above, the present invention contemplates line 22 passing between outer plate 20 and inner plate 18 from below or in any other suitable manner. Furthermore, although a single line 22 is described, the present invention contemplates multiple lines providing the functionality of line 22. For example, two lines, one on each side of device 10, may cooperate to provide the functionality of line 22.

Lower arch 14 includes two or any other suitable number of hooks or other attachment sites 28 embedded in or otherwise coupled to lower arch 14. In one embodiment, although hooks 28 may extend outwardly from lower arch 14 to some extent, hooks 28 are substantially continuous with the surface of lower arch 14. Line 22 includes loops or other appropriate attachment mechanisms 30 at or near its ends for removably engaging hooks 28 and thus lower arch 14. Although FIG. 1 shows a single set of hooks 28, the present invention contemplates multiple sets of hooks or other attachment sites 28 such that each loop 30 may engage any one of multiple hooks 28 according to particular needs. In one embodiment, when loops 30 have engaged hooks 28 and device 10 is inserted into the user's mouth, line 22 and hooks 28 do not interfere with or otherwise irritate the soft tissues of the user's mouth, providing increased comfort and an important technical advantage.

Another important technical advantage of the present invention is the ease with which device 10 may be fitted and adjusted. After loops 30 of line 22 have engaged hooks 28 of lower arch 14 and central portion 26 of line 22 has been passed between inner plate 18 and outer plate 20, line 22 may be moved as appropriate to adjustably position lower arch 14 forwardly relative to upper arch 12, thereby allowing the user's breathing passage to open more fully and allowing the user to breath more easily through the user's nose and mouth. After determining the desired position of the of lower arch 14 with respect to upper arch 12, screws 24 or other appropriate fasteners are tightened to secure line 22 between outer plate 20 and inner plate 18 and maintain the desired position of lower arch 14. After adjusting lower arch 14 to its desired position, any excess central portion 26 of line 22, hanging below, protruding above, or otherwise extending from between inner plate 18 and outer plate 20 may be cut or otherwise removed such that line 22 does not interfere with the natural position of the user's tongue or the ability of the user to close the user's mouth. Although central portion 26 of line 22 is shown extending below inner plate 18 and outer plate 20, the present invention contemplates central portion 26 extending above, below, to the side of, or with any other appropriate relationship to inner plate 18 and outer plate 20.

Subsequent adjustments to the position of lower arch 14 may be made by temporarily loosening outer plate 20, adjusting line 22 forward or backward according to the user's particular needs, and resecuring line 22 between outer plate 20 and inner plate 18 to maintain the desired position of the lower arch 14. If after this further adjustment portions of line 22 extend beyond inner plate 18 and outer plate 20, the excess line 22 may be cut or otherwise removed. On the other hand, if after further adjustment line 22 is too short to properly secure using inner plate 18 and outer plate 20 due to the cutting of line 22, a replacement line may be attached, adjusted, and secured in the manner described above for the initial positioning of lower arch 14. As with the initial line 22, the replacement line 22 may be subsequently adjusted according to particular needs. Adjustment of device 10 in the manner described above may be performed by a clinical professional or by the user, potentially decreasing the cost of device 10 to the user.

Figure 2A:
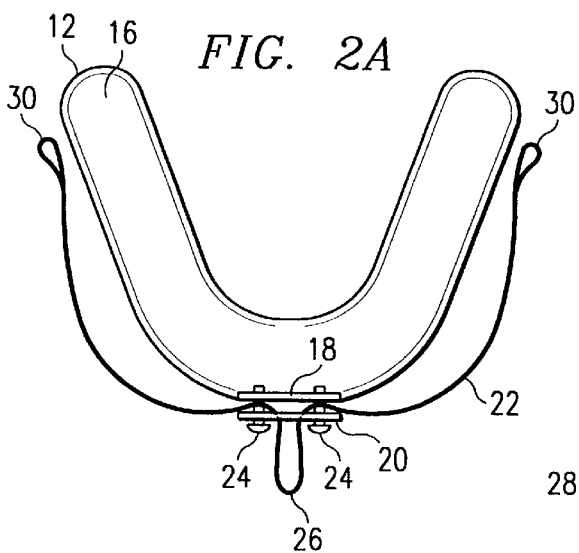
FIGS. 2A, 2B, 4A, and 4B illustrate exemplary upper and lower arches according to the present invention.
Figure 2B:
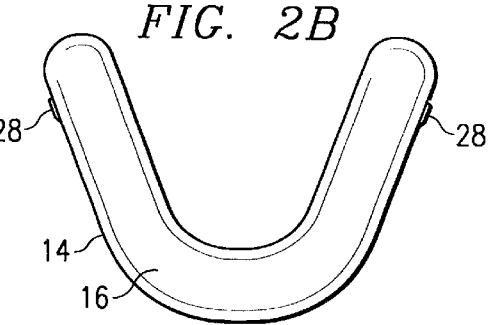

FIGS. 2A and 2B illustrate upper arch 12 and lower arch 14, respectively. As described above and further illustrated in FIG. 2A, when line 22 is secured and device 10 is inserted into the user's mouth, outer plate 20 may be secured to inner plate 18 such that outer plate 20 is substantially continuous with the surface of upper arch 12. For example, only and not by way of limitation, outer plate 20 may extend less than approximately 1 mm from the surface of upper arch 12 when outer plate 20 is secured to inner plate 18. In one embodiment, the arrangement of outer plate 20 with respect to upper arch 12 allows all of the components of device 10 to be contained within the user's mouth, prevents the natural position of the user's upper lip and inner mouth from being significantly disturbed, and allows the user's mouth to be substantially closed while device 10 is in the user's mouth, thus increasing the comfort to the user. Furthermore, in one embodiment, as described above and further illustrated in FIG. 2B, hooks 28 are substantially continuous with the surface of lower arch 14 such that soft tissues of the user's mouth are not significantly disturbed, making device 10 more comfortable to the user when inside the user's mouth.

Figure 3:
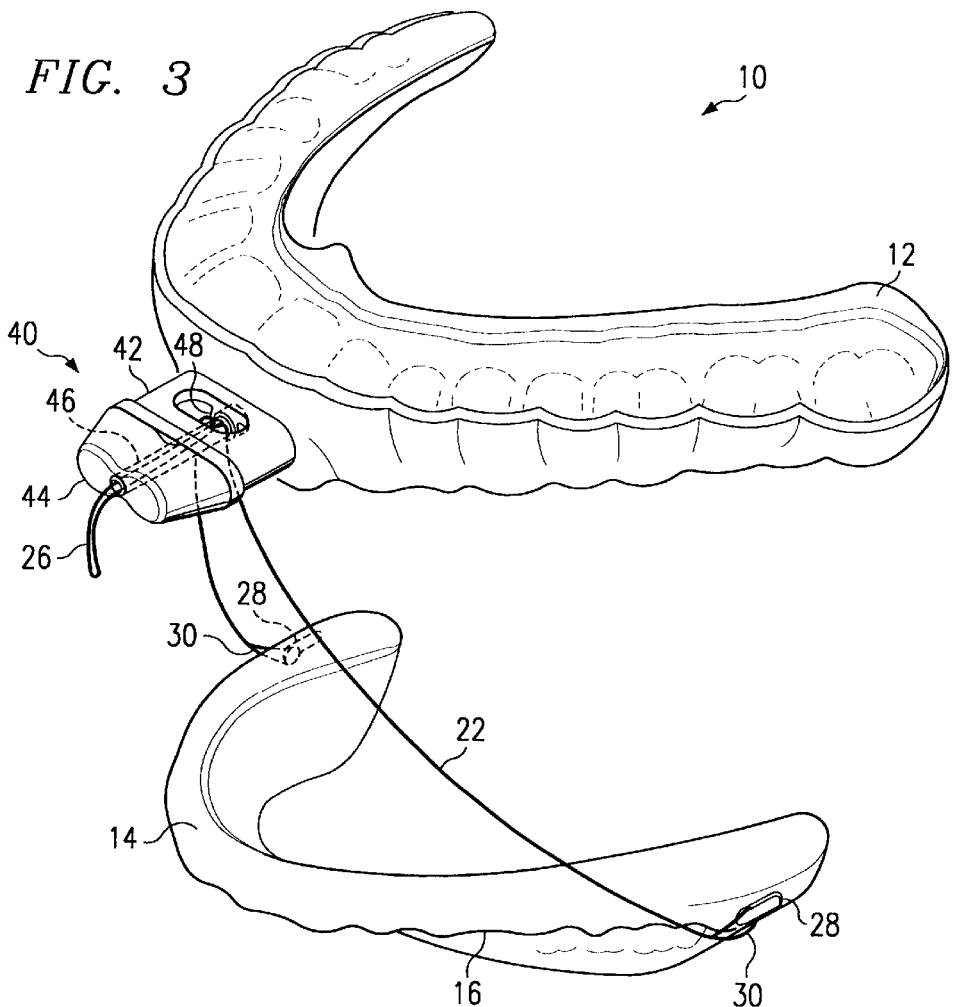
Figure 4A:
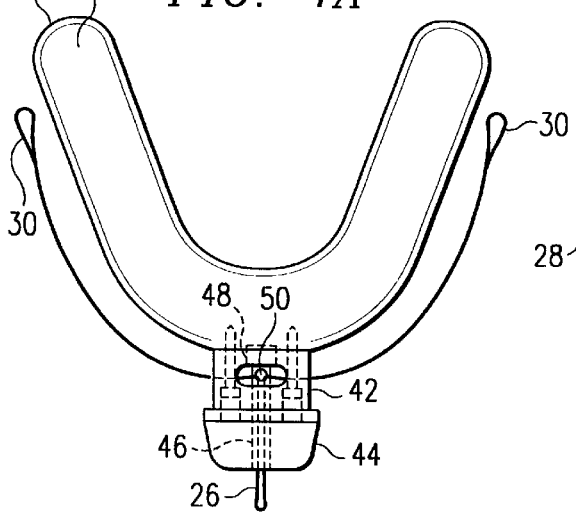
Figure 4B:
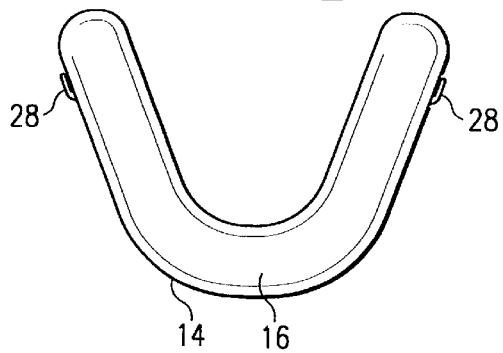

FIG. 3 illustrates an alternative embodiment of the present invention that includes an adjustor 40 having a body 42 that is integral to or separate from upper arch 12. Adjustor 40 also includes a rotating portion 44 that rotates relative to body 42 when appropriate pressure is applied to rotating portion 44 during the fitting or adjustment of device 10. Rotating portion 44 includes a shaft 46 coupling rotating portion 44 to body 42 or to upper arch 12 at attachment housing 48. Shaft 46 may be any stainless steel, aluminum, or other suitable shaft that is embedded or otherwise fixed to rotating portion 44, but is permitted to rotate relative to attachment housing 48. FIGS. 4A and 4B illustrate upper arch 12 and lower arch 14, respectively.

In one embodiment, shaft 46 has at least one opening 50 (best seen in FIG. 4A) and is substantially hollow to receive central portion 26 of line 22. When line 22 is inserted into shaft 46 through the opening and rotating portion 44 is rotated, line 22 is successively wrapped around shaft 46 to decrease the effective length of line 22 and adjust lower arch 14 forward. In a similar manner, rotation of rotating portion 44 in the opposite direction adjusts lower arch 14 rearward. Body 42 may include a cavity of suitable size and configuration to permit loops 30 of line 22 to pass through body 42 as central portion 26 of line 22 is being inserted into shaft 46, or afterwards when loops 30 of line 22 are engaging hooks 28 of lower arch 14. The cavity may also contribute to the ability of shaft 46 to continue rotating when line 22 has been already wrapped around shaft 46 one or more times, thereby increasing the effective diameter of shaft 46. If central portion 26 of line 22 extends forward from rotating portion 44 after fitting or subsequent adjustment of lower arch 14, central portion 26 may be cut or otherwise removed according to particular needs.

In another embodiment, shaft 46 includes a hook to engage line 22 and allow it to be wrapped around shaft 46 when rotating portion 44 is rotated. The present invention contemplates removably coupling line 22 to shaft 46 in any suitable manner. According to the present invention, line 22 may be coupled to shaft 46 and wrapped around shaft 46 to adjust lower arch 14 forward to a desired position. Line 22 may be unwrapped from shaft 46 to adjust lower arch 14 rearward to a desired position or may be further wrapped around shaft 46 to further adjust lower arch 14 forward. Using line 22, shaft 46, and rotating portion 44, lower arch 14 may be readily adjusted and repeatedly readjusted to provide optimal fit and performance. In one embodiment, although at least a portion of adjustor 40 extends forward from the user's mouth, device 10 still does not substantially interfere with the natural position of the user's lips or inner mouth, such that device 10 remains comfortable for the user.

Figure 5:
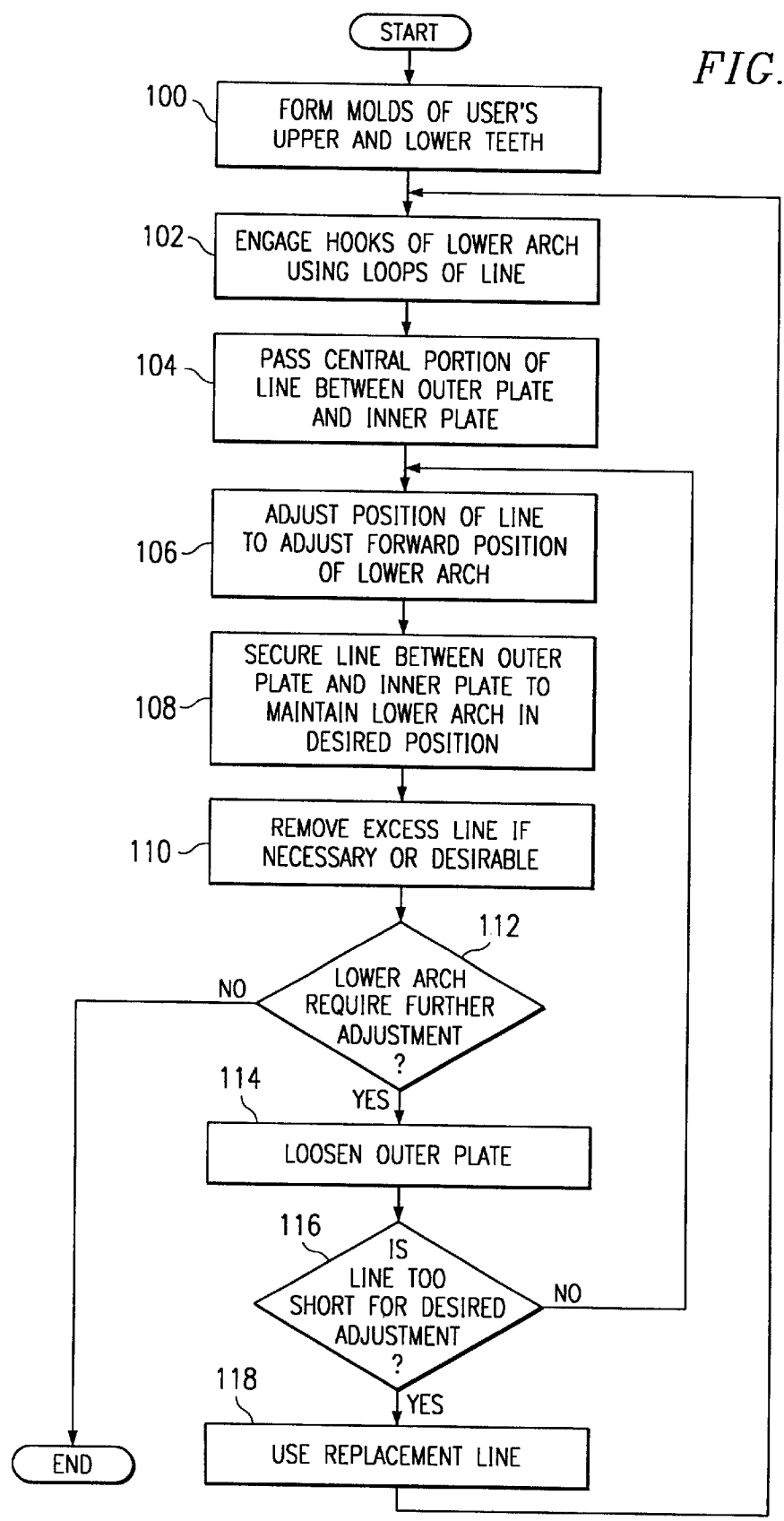

FIG. 5 illustrates an exemplary method of fitting device 10 according to the present invention. The method begins at step 100, where molds of at least some of the user's upper and lower teeth are formed in upper arch 12 and lower arch 14, respectively. At step 102, loops 30 of line 22 engage hooks 28 of lower arch 14 and, at step 104, central portion 26 of line 22 is passed between inner plate 18 and outer plate 20. At step 106, line 22 is moved between inner plate 18 and outer plate 20 to adjustably position lower arch 14 and, at step 108, line 22 is secured between inner plate 18 and outer plate 20 to maintain lower arch 14 in the desired position. At step 110, any excess line 22 extending from between inner plate 18 and outer plate 20 may be removed if necessary or desirable. If lower arch 14 requires no further adjustment at step 112, during the same fitting session or at any time in the future, the method ends.

On the other hand, if further adjustment of lower arch 14 is desired at step 112, during the same fitting session or at any time in the future, outer plate 20 is loosened at step 114. If line 22 is too short for the desired adjustment at step 116, a replacement line 22 may be used at step 118, and the method returns to step 102. If line 22 is not too short for the desired adjustment at step 116, the method returns to step 106. The method may continue in this manner indefinitely until lower arch 14 requires no further adjustment at step 112 and the method ends. The steps of the method may be performed in any appropriate order. The method may be performed by a clinical professional, by the user, or by both a clinical professional and a user at different times, providing an important technical advantage. For example, a clinical professional may perform the initial fitting and the user may perform any subsequent adjustments.

FIG. 6 illustrates an alternative method of fitting device 10 according to the present invention. The method begins at step 200, where molds of at least some of the user's upper and lower teeth are formed in upper arch 12 and lower arch 14, respectively. At step 202, central portion 26 of line 22 is inserted into shaft 46. Alternatively, as described above, central portion 26 may hook onto or otherwise couple to shaft 46. At step 204, loops 30 of line 22 are passed through body 42 of adjustor 44 and, at step 206, loops 30 engage hooks 28 of lower arch 14. Rotating portion 44 of adjustor 40 is rotated in an appropriate direction at step 208 to wrap line 22 around shaft 46 and adjust lower arch 14 forward. At step 210, any excess line 22 extending forward from shaft 46 may be removed if necessary or desirable.

If lower arch 14 requires no further adjustment at step 212, during the same fitting session or at any time in the future, the method ends. On the other hand, if further adjustment of lower arch 14 is desired at step 212, during the same fitting session or at any time in the future, rotating portion 44 of adjustor 40 is rotated as appropriate. The method may continue in this manner indefinitely until lower arch 14 requires no further adjustment at step 212 and the method ends. The steps of the method may be performed in any appropriate order. The method may be performed by a clinical professional, by the user, or by both a clinical professional and a user at different times, providing an important technical advantage. As an example, a clinical professional may perform the initial fitting and the user may perform any subsequent adjustments. Line 22 may be replaced if it breaks, becomes worn, or is too short, either at its original length or after cutting, to allow desired rearward adjustment of lower arch 14.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving the breathing of a user, comprising:
   an upper arch adapted to receive at least some of the user's upper teeth;
   a plate coupled to the upper arch;
   a lower arch adapted to receive at least some of the user's lower teeth; and
   a line adapted to removably engage at least one attachment site of the lower arch and to move between the plate and the upper arch to adjust a forward position of the lower arch relative to the upper arch, the plate adapted to secure the line between the plate and the upper arch to at least temporarily fix the forward position of the lower arch relative to the upper arch.

2. The device of claim 1, wherein the line comprises at least one loop and the lower arch comprises at least one hook to receive the loop.

3. The device of claim 1, wherein the line comprises a braided stainless steel line.

4. The device of claim 1, wherein the upper arch comprises an inner plate, the line adapted to be secured between the plate and the inner plate.

5. The device of claim 1, wherein the plate is substantially continuous with a surface of the upper arch.

6. The device of claim 1, wherein the line is adapted to removably engage first and second attachment sites of the lower arch at first and second ends of the line, respectively, the line adapted to be secured between the plate and the upper arch between the first and second ends.

7. The device of claim 1, wherein the device allows the user's mouth to substantially close.

8. The device of claim 1, wherein the device does not obstruct the user's breathing passage and does not interfere with the user's tongue.

9. A device for improving the breathing of a user, comprising:
   an outer plate;
   an upper arch comprising an inner plate and adapted to receive at least some of the user's upper teeth;
   a lower arch adapted to receive at least some of the user's lower teeth;
   a line adapted to removably engage at least one attachment site of the lower arch and to move between the inner and outer plates to adjust a forward position of the lower arch relative to the upper arch;
   the outer plate adapted to secure the line between the outer plate and the inner plate to at least temporarily fix the forward position of the lower arch relative to the upper arch, the outer plate being substantially continuous with a surface of the upper arch, the device preventing the user's lips and inner mouth from being significantly disturbed and allowing the user's mouth to substantially close.

10. The device of claim 9, wherein:
    the lower arch comprises a first hook and a second hook at the first and second attachment sites, respectively;
    the line comprises a first loop and a second loop adapted to removably engage the first hook and the second hook, respectively; and
    the line is adapted to be secured between the inner and outer plates between the first and second loops.

11. A device for improving the breathing of a user, comprising:
    a lower arch adapted to receive at least some of the user's lower teeth;
    a line comprising ends adapted to removably engage at least one attachment site of the lower arch;
    an upper arch adapted to receive at least some of the user's upper teeth; and
    an adjustor coupled to the upper arch and comprising a shaft, the shaft having a channel aligned in a forward direction relative to the upper arch and adapted to receive a portion of the line that is inserted into the channel, at least a portion of the adjustor rotatable in a first direction to wrap the line around the shaft and thereby adjust the lower arch in the forward direction relative to the upper arch.

12. The device of claim 11, wherein the line comprises at least one loop and the lower arch comprises at least one hook to receive the loop.

13. The device of claim 11, wherein the line comprises a braided stainless steel line.

14. The device of claim 11, wherein:

the line removably engages the lower arch at first and second ends of the line; and the line is wrapped around the shaft between the first and second ends.

15. The device of claim 11, wherein the portion of the adjustor is operable to rotate in a second direction opposite the first direction to adjust the lower arch in a rearward direction relative to the upper arch.

16. A method of fitting an oral appliance to a user, comprising:

inserting an upper arch into the user's mouth, the upper arch coupled to a plate and adapted to receive at least some of the user's upper teeth;

inserting a lower arch into the user's mouth, the lower arch adapted to receive at least some of the user's lower teeth;

removably engaging at least one attachment site of the lower arch using a line;

moving the line between the plate and upper arch to adjust a forward position of the lower arch relative to the upper arch; and securing the line between the plate and the upper arch to at least temporarily fix the forward position of the lower arch relative to the upper arch.

17. The method of claim 16, further comprising receiving one or more loops of the line using one or more hooks of the lower arch.

18. The method of claim 16, wherein the line comprises a braided stainless steel line.

19. The method of claim 16, wherein the upper arch comprises an inner plate and securing the line comprises securing the line between the plate and the inner plate.

20. The method of claim 16, wherein:

the line removably engages the lower arch at first and second ends of the line; and the line is secured to the upper arch between the first and second ends.

21. The method of claim 16, further comprising allowing the user's mouth to substantially close.

22. The method of claim 16, wherein the plate is substantially continuous with a surface of the upper arch such that the user's upper lip and inner mouth are not significantly disturbed.

23. A method of fitting an oral appliance, comprising:

inserting a lower arch into the user's mouth, the lower arch adapted to receive at least some of the user's lower teeth;

inserting an upper arch into the user's mouth, the upper arch adapted to receive at least some of the user's upper teeth, the upper arch comprising an adjustor having a shaft with a channel aligned in a forward direction relative to the upper arch;

inserting a portion of a line into the channel;

removably engaging the lower arch using the line; and rotating at least a portion of the adjustor in a first direction to wrap the line around the shaft, thereby adjusting the lower arch in the forward direction relative to the upper arch.

24. The method of claim 23, further comprising forming a mold of at least some of the user's teeth using a deformable material.

25. The method of claim 23, further comprising receiving one or more loops of the line using one or more hooks of the lower arch.

26. The method of claim 23, wherein the line comprises a braided stainless steel line.

27. The method of claim 23, wherein:

the line removably engages the lower arch at first and second ends of the line; and the line is wrapped around the shaft between the first and second ends.

28. The method of claim 23, further comprising rotating the portion of the adjustor in a second direction opposite the first direction to adjust the lower arch in a rearward direction relative to the upper arch.

* * * * *